US009358198B2

(12) United States Patent
Sato et al.

(10) Patent No.: US 9,358,198 B2
(45) Date of Patent: Jun. 7, 2016

(54) DYEING OF KERATIN FIBERS USING INDOLE ANALOGUE

(75) Inventors: Yukihide Sato, Kakamigahara (JP); Yoshihiko Hirose, Kakamigahara (JP)

(73) Assignee: AMANO ENZYME INC., Nagoya-Shi (JP)

( * ) Notice: Subject to any disclaimer, the term of this patent is extended or adjusted under 35 U.S.C. 154(b) by 0 days.

(21) Appl. No.: 14/369,500

(22) PCT Filed: Jan. 4, 2012

(86) PCT No.: PCT/JP2012/050043
§ 371 (c)(1),
(2), (4) Date: Jun. 27, 2014

(87) PCT Pub. No.: WO2013/099296
PCT Pub. Date: Jul. 4, 2013

(65) Prior Publication Data
US 2014/0359950 A1    Dec. 11, 2014

(30) Foreign Application Priority Data

Dec. 29, 2011   (WO) ................. PCT/JP2011/080529

(51) Int. Cl.
| | | |
|---|---|---|
| *A61K 8/49* | (2006.01) | |
| *A61K 8/66* | (2006.01) | |
| *A61Q 5/10* | (2006.01) | |
| *C12N 9/02* | (2006.01) | |
| *A61K 8/99* | (2006.01) | |

(52) U.S. Cl.
CPC ............... *A61K 8/4913* (2013.01); *A61K 8/492* (2013.01); *A61K 8/66* (2013.01); *A61K 8/99* (2013.01); *A61Q 5/10* (2013.01); *C12N 9/001* (2013.01); *C12Y 103/03005* (2013.01); *A61K 2800/10* (2013.01)

(58) Field of Classification Search
CPC ............ A61Q 5/10; A61K 2800/4322; A61K 2800/4324; A61K 2800/43; A61K 8/4913; A61K 8/66; A61K 8/492; C12N 9/001; C12Y 103/03005
USPC .............................................. 8/405, 406, 408
See application file for complete search history.

(56) References Cited

U.S. PATENT DOCUMENTS

| 6,152,967 A | 11/2000 | Maubru |
| 6,730,133 B1 | 5/2004 | Plos et al. |
| 6,958,080 B2 * | 10/2005 | Mitamura et al. ................. 8/401 |
| 2003/0103917 A1 | 6/2003 | Pruche |
| 2004/0064901 A1 | 4/2004 | Kleen |
| 2006/0277694 A1 * | 12/2006 | Kleen et al. ....................... 8/405 |
| 2009/0117638 A1 | 5/2009 | Kumita et al. |
| 2013/0078662 A1 | 3/2013 | Mano et al. |

FOREIGN PATENT DOCUMENTS

| FR | 2768617 A1 | 7/1999 |
| JP | 2000-502757 A | 3/2000 |
| JP | 2000-516264 A | 12/2000 |
| JP | 2004-089042 A | 3/2004 |
| JP | 2004089042 A | 3/2004 |
| JP | 2004-510798 A | 4/2004 |
| JP | 2004-522709 A | 7/2004 |
| JP | 2006-068003 A | 3/2006 |
| JP | 2007-326809 A | 12/2007 |
| JP | 2008-161178 A | 7/2008 |
| JP | 2009-137877 A | 6/2009 |
| JP | 4743854 B2 | 8/2011 |
| WO | WO-97/23684 A1 | 7/1997 |
| WO | WO 9723685 A1 | 7/1997 |
| WO | WO-00/32158 A1 | 6/2000 |
| WO | WO-02/22095 A1 | 3/2002 |
| WO | WO-2011/117839 A1 | 9/2011 |

OTHER PUBLICATIONS

Sakasegawa et al. "Billirubin Oxidase Activity of Bacillus Subtilis CotA", App. Environ. Microbiol., vol. 72, No. 1, Jan. 2006, pp. 972-975.*
S. Sakasegawa et al. "Bilirubin Oxidase Activity of *Bacillus subtilis* CotA", Applied and Environmental Microbiology, Jan. 2006, vol. 72, No. 1, pp. 972-975 and a cover page.
Supplementary European Search Report dated Jan. 8, 2014, issued for the corresponding European patent application No. 12808238.5.
Communication dated Feb. 25, 2014, issued for the corresponding European application No. 12808238.5.
International Search Report dated Apr. 17, 2012, issued for PCT/JP2012/050043.
International Search Report dated Apr. 17, 2012, issued for PCT/JP2011/080529.
French Search Report, issued Nov. 3, 2015.

\* cited by examiner

*Primary Examiner* — Amina Khan
(74) *Attorney, Agent, or Firm* — Locke Lord, LLP; James E. Armstrong, IV; Nicholas R. Herrel (57) ABSTRACT

The problem is to provide a means for effectively dyeing keratin fibers while retaining high safety. Provided are a dyeing method and a dyeing agent, which include a combination of an oxidation dyeing agent consisting of an indole analog and a bilirubin oxidase derived from *Myrothecium verrucaria* or *Bacillus Subtilis*.

14 Claims, 1 Drawing Sheet

DYEING OF KERATIN FIBERS USING INDOLE ANALOGUE

TECHNICAL FIELD

The present invention relates to dyeing of keratin fibers. Specifically, the present invention relates to a dyeing agent and a dyeing method utilizing an indole analogue as an oxidation dye.

BACKGROUND ART

Dyeing methods utilizing oxidation dyeing agents such as phenylenediamines and aminophenols are frequently used in dyeing of keratin fibers, specifically human hairs and the like, by utilizing the advantages that dyeing is possible in various color tones, lasts long, and doesn't take much time, and the like. On the other hand, indole analogues are also utilized as oxidation dyeing agents for dyeing keratin. For example, an indole derivative 5,6-dihydroxyindole is a melanin precursor and polymerizes in the presence of oxygen to form a melanin pigment. It is possible to dye hairs and the like by utilizing this reaction. For example, Patent Documents 1 and 2 disclose air oxidation-type dyeing agents utilizing indole derivatives such as 5,6-dihydroxyindole.

CITATION LIST

Patent Documents

Patent Document 1: JP 2007-326809 A
Patent Document 2: JP 2009-137877 A
Patent Document 3: JP 2004-510798 W
Patent Document 4: Japanese Patent No. 4743954

SUMMARY OF INVENTION

Technical Problem

It can be considered that indole analogues such as 5,6-dihydroxyindole are highly safe as compared to oxidation dyeing agents such as phenylenediamines and aminophenols. However, there is a specific problem that the dyeing effect thereof is low. Therefore, the present invention aims at providing a dyeing method that can exert a high dyeing effect while ensuring high safety by utilizing an indole analogue as an oxidation dye, and a dyeing agent used therefor.

Solution to Problem

The present inventors focused on a bilirubin oxidase (hereinafter abbreviated as "BO"), which is a kind of oxidation enzyme, and considered the possibility of application to hair dyeing utilizing an indole analogue as an oxidation dye. As a result, it was found that the BO provides a high dyeing effect. Furthermore, they succeeded in identifying BOs having extremely high effectiveness (i.e., BOs that give specifically high dyeing effects) by comparative experiments using various BOs. The inventions shown below are mainly based on these efforts. Although Patent Document 3 listed above that discloses a method for dyeing keratin fibers shows a BO as an oxidation enzyme and an indole analogue as an oxidation dye, it fails to specifically describe the case when these are used in combination (for example, experimental data), and thus it is completely unclear whether or not the combination use of these is actually effective for dyeing keratin fibers. Furthermore, the literature does not mention at all about the specific BOs found by the present inventors.

[1] A dyeing agent for dyeing keratin fibers, comprising a bilirubin oxidase (EC1.3.3.5) derived from *Myrothecium verrucaria* or *Bacillus Subtilis*.

[2] The dyeing agent according to [1], wherein the bilirubin oxidase is consisting of a protein described in any of the following (1) to (9):

(1) a protein consisting of the amino acid sequence of SEQ ID NO: 2;

(2) a protein consisting of an amino acid sequence in which one or several amino acid(s) is/are mutated, deleted or added in the amino acid sequence of SEQ ID NO: 2, which has a bilirubin oxidase activity;

(3) a protein that is encoded by the polynucleotide of SEQ ID NO: 1;

(4) a protein consisting of the amino acid sequence of SEQ ID NO: 4;

(5) a protein consisting of an amino acid sequence in which one or several amino acid(s) is/are mutated, deleted or added in the amino acid sequence of SEQ ID NO: 4, which has a bilirubin oxidase activity;

(6) a protein that is encoded by the polynucleotide of SEQ ID NO: 3;

(7) a protein consisting of the amino acid sequence of SEQ ID NO: 6;

(8) a protein consisting of an amino acid sequence in which one or several amino acid(s) is/are mutated, deleted or added in the amino acid sequence of SEQ ID NO: 6, which has a bilirubin oxidase activity;

(9) a protein that is encoded by the polynucleotide of SEQ ID NO: 5.

[3] The dyeing agent according to [1] or [2], wherein the keratin fibers are human hairs.

[4] The dyeing agent according to any one of [1] to [3], which is a combination with an oxidation dyeing agent consisting of an indole derivative or an indoline derivative.

[5] The dyeing agent according to [4], wherein the oxidation dyeing agent is an oxidation dyeing agent selected from the group consisting of 5,6-dihydroxyindole, 5,6-dihydroxyindoline, 5,6-dihydroxyindole-2-carboxylic acid, 5,6-dihydroxyindoline-2-carboxylic acid, 4-aminoindole and 5-aminoindole.

[6] The dyeing agent according to [4] or [5], which is a one-component form containing the oxidation dyeing agent and the bilirubin oxidase.

[7] The dyeing agent according to [4] or [5], which is a two-component type consisting of a first element containing the oxidation dyeing agent and a second element containing the bilirubin oxidase.

[8] A dyeing method, comprising a step of treating keratin fibers with the dyeing agent according to any one of [1] to [7].

[9] The dyeing method according to [8], wherein the treatment is conducted under a condition of pH 7.0 to 8.0.

DESCRIPTION OF EMBODIMENTS

1. Dyeing Agent

The first aspect of the present invention relates to a dyeing agent that is used for dyeing keratin fibers (human hairs, hairs or the like of, for example, cows, horses, sheep, goats, alpacas, and Angora rabbits). The dyeing agent of the present invention contains a bilirubin oxidase (BO) (EC1.3.3.5), which is an oxidation enzyme. The dyeing agent of the present invention acts on an oxidation dye to exert a desired dyeing effect. Therefore, the dyeing agent of the present invention is typically used in combination with an oxidation dye. In the present specification, the expression "used in combination" or "is a combination with" refers to that the oxidation dye and BO are used in combination. In an exemplary embodiment, the dyeing agent of the present invention is provided as a composition in which the oxidation dye and BO are mixed. The dyeing agent of this embodiment is referred to as a one-component type dyeing agent. On the other hand, it is also possible to provide the dyeing agent of the present invention in the form of a kit comprising a first element containing the oxidation dye and a second element containing BO. The dyeing agent of this embodiment is referred to as a two-component type dyeing agent. In the case of the two-component type dyeing agent, the respective elements are provided in a state of being housed in separated containers or compartments, and the two elements are mixed to be used. It can be said that the one-component type dyeing agent is superior to the two-component type dyeing agent in that it has a simple constitution and can attain an easier usage.

(1) Dye

In the present specification, the term "oxidation dye" refers to a dye that requires an oxidation reaction for color development or dyeing. The oxidation dye includes "a dye precursor" that develops a color by the polymerization of the precursor itself, and "a dye aid (coupler)" that exhibits an inherent color tone by being polymerized with a dye precursor. In the present invention, an indole analogue is used as the oxidation dye. Various indole analogues can be used. Preferably, a suitable oxidation dye is adopted among compounds that fall within an indole derivative or an indoline derivative, or a salt thereof (for example, an acid addition salt including a hydrochloride, a hydrobromide, a sulfate, a tartrate, a lactate or an acetate, or the like). Specific examples of the indole derivative and indoline derivative are 5,6-dihydroxyindoline, N-methyl-5,6-dihydroxyindoline, N-ethyl-5,6-dihydroxyindoline, N-butyl-5,6-dihydroxyindoline, 4-hydroxy-5-methoxyindoline, 6-hydroxy-7-methoxyindoline, 6,7-dihydroxyindoline, 4,5-dihydroxyindoline, 4-methoxy-6-hydroxyindoline, N-hexyl-5,6-dihydroxyindoline, 2-methyl-5,6-dihydroxyindoline, 3-methyl-5,6-dihydroxyindoline, 4-hydroxyindoline, 2,3-dimethyl-5,6-dihydroxyindoline, 2-methyl-5-ethyl-6-hydroxyindoline, 2-methyl-5-hydroxy-6-β-hydroxyethylindoline, 4-hydroxypropylindoline, 2-hydroxy-3-methoxyindoline, 6-hydroxy-5-methoxyindoline, 6-hydroxyindoline, 5-hydroxyindoline, 7-hydroxyindoline, 7-aminoindoline, 5-aminoindoline, 4-aminoindoline, 5,6-dihydroxyindoline-2-carboxylic acid, 1-methyl-5,6-dihydroxyindoline, 4,5-dihydroxyindole, 5,6-dihydroxyindole, 6,7-dihydroxyindole, N-methyl-5,6-dihydroxyindole, N-ethyl-5,6-dihydroxyindole, N-hexyl-5,6-dihydroxyindole, 2-methyl-5,6-dihydroxyindole, 3-methyl-5,6-dihydroxyindole, 4-hydroxyindole, 2,3-dimethyl-5,6-dihydroxyindole, 2-methyl-5-ethyl-6-hydroxyindole, 2-methyl-5-hydroxy-6-β-hydroxyethylindole, 4-hydroxypropylindole, 2-hydroxy-3-methoxyindole, 4-hydroxy-5-methoxyindole, 6-hydroxy-7-methoxyindole, 6-hydroxy-5-methoxyindole, 6-hydroxyindole, 5-hydroxyindole, 7-hydroxyindole, 7-aminoindole, 6-aminoindole, 5-aminoindole, 4-aminoindole, 5,6-dihydroxyindole-2-carboxylic acid, and 1-methyl-5,6-dihydroxyindole. In a preferable exemplary embodiment, one or two kinds of oxidation dyeing agent(s) selected from the group consisting of 5,6-dihydroxyindole, 5,6-dihydroxyindoline, 5,6-dihydroxyindole-2-carboxylic acid, 5,6-dihydroxyindoline-2-carboxylic acid, 4-aminoindole and 5-aminoindole is/are used.

One or two kinds of oxidation dye(s) is/are used for the dyeing agent of the present invention. Combination use of two or more kinds of oxidation dyes is effective for improving the dyeing effect, adjusting the color (color tone), and the like. Specifically, it is preferable to use an oxidation dye that is classified into a dye precursor and an oxidation dye that is classified into a dye aid in combination.

The incorporation amount of the oxidation dye is not specifically limited, and the incorporation amount may be determined with consideration for the characteristic of the oxidation dye used, intended purposes, and the like. In the case of the one-component type dyeing agent, the oxidation dye can be incorporated so as to be, for example, 0.01 to 20% by weight, preferably 0.05 to 10% by weight, further preferably 0.01 to 1% by weight, with respect to the whole amount of the dyeing agent. In the case of the two-component type dyeing agent, the oxidation dye can be incorporated so as to be, for example, 0.01 to 20% by weight, preferably 0.05 to 10% by weight, further preferably 0.01 to 1% by weight, with respect to the whole amount of the first element in which the oxidation dye is to be contained.

As a component that contributes to dyeing, a direct dye may be incorporated in addition to the oxidation dye. By incorporating the direct dye, the dyeing effect can be enhanced and the color tone of the dyeing can be adjusted. Examples of the direct dye include 2-amino-4-nitrophenol, 2-amino-5-nitrophenol, 1-amino-4-methylaminoanthraquinone, nitro-p-phenylenediamine hydrochloride, 1,4-diaminoanthraquinone, nitro-p-phenylenediamine, picramic acid, sodium picramate, 2-amino-5-nitrophenol sulfate, resorcinol, nitro-p-phenylenediamine sulfate, p-nitro-o-phenylenediamine sulfate, p-nitro-m-phenylenediamine sulfate, Natural Orange 6 (2-hydroxy-1,4-naphthoquinone), Acid Orange 8, Acid Violet 17, Remazol Brilliant Blue, Evans Blue and Acid Blue 80.

The incorporation amount of the direct dye is also not specifically limited. In the case of the one-component type dyeing agent, the direct dye can be incorporated so as to be, for example, 0.01 to 20% by weight with respect to the whole amount of the dyeing agent. In the case of the two-component type dyeing agent, the direct dye is incorporated in the first element in which the oxidation dye is to be contained and/or the second element in which the BO is to be contained. The incorporation amount in this case is, for example, 0.01 to 20% by weight with respect to the whole amount of the first element, or for example, 0.01 to 20% by weight with respect to the whole amount of the second element. In addition, two or more kinds of direct dyes can be used in combination in the same manner as in the oxidation dyes.

(2) Enzyme

In the present invention, an oxidation enzyme BO is used. Specifically, a BO derived from *Myrothecium verrucaria* or a BO derived from *Bacillus Subtilis* is used. In other words, the original producing bacterium for the BO used in the present invention is *Myrothecium verrucaria* or *Bacillus Subtilis*. The producing bacterium may be a wild strain (a strain separated from the nature, which has not been subjected to a mutation or modification treatment such as genetic engineering) or a mutant strain. A BO that is produced by a transformant obtained by introducing the BO gene of *Myrothecium verrucaria* into a host microorganism also falls within a BO derived from *Myrothecium verrucaria*. The same applies to the BO derived from *Bacillus Subtilis*. As mentioned above, a BO that is produced by a gene recombination technique (recombinant BO) may also be used.

Specific examples of the producing bacterium for the BO used in the present invention include *Myrothecium verrucaria* MT-1 (FERM-BP 653 (see Agricultural and Biological Chemistry, Vol. 45, p. 2383-2384 (1981))), *Myrothecium verrucaria* IFO 6113, *Myrothecium verrucaria* IFO 6133, *Myrothecium verrucaria* IFO 6351, *Myrothecium verrucaria* IFO 9056 and *Bacillus Subtilis* ATCC 23857 strains. A purified preparation of a bilirubin oxidase can be obtained by liquid-culturing or solid-culturing these strains by a conventional method, and conducting extraction, salting-out, dialysis, ion exchange, gel permeation or the like from the culture liquid.

The amino acid sequence of the BO derived from *Myrothecium verrucaria* MT-1 strain is shown in SEQ ID NO: 2 (full length, including signal sequence) and SEQ ID NO: 4 (full length, signal sequence is not included). In an exemplary embodiment of the present invention, a BO consisting of a protein according to any of the following (1) to (6) is used. Meanwhile, the sequence of SEQ ID NO: 1 is a gene sequence that encodes the amino acid sequence of SEQ ID NO: 2, and the sequence of SEQ ID NO: 3 is a gene sequence that encodes the amino acid sequence of SEQ ID NO: 4.

(1) a protein consisting of the amino acid sequence of SEQ ID NO: 2;
(2) a protein consisting of an amino acid sequence in which one or several amino acid(s) is/are mutated, deleted or added in the amino acid sequence of SEQ ID NO: 2, which has a bilirubin oxidase activity;
(3) a protein that is encoded by the polynucleotide of SEQ ID NO: 1;
(4) a protein consisting of the amino acid sequence of SEQ ID NO: 4;
(5) a protein consisting of an amino acid sequence in which one or several amino acid(s) is/are mutated, deleted or added in the amino acid sequence of SEQ ID NO: 4, which has a bilirubin oxidase activity;
(6) a protein that is encoded by the polynucleotide of SEQ ID NO: 3.

The BO derived from *Bacillus Subtilis* ATCC 23857 strain is a component protein in the sporoderm, and typically has the amino acid sequence of SEQ ID NO: 6. Therefore, in an exemplary embodiment of the present invention, a BO consisting of a protein according to any of the following (7) to (9) is used. Meanwhile, the sequence of SEQ ID NO: 5 is a gene sequence that encodes the amino acid sequence of SEQ ID NO: 6.

(7) a protein consisting of the amino acid sequence of SEQ ID NO: 6;
(8) a protein consisting of an amino acid sequence in which one or several amino acid(s) is/are mutated, deleted or added in the amino acid sequence of SEQ ID NO: 6, which has a bilirubin oxidase activity;
(9) a protein that is encoded by the polynucleotide of SEQ ID NO: 5.

For the details of the BO derived from *Bacillus Subtilis*, Patent Document 4 (Japanese Patent No. 4743854) can be referred to.

The BO derived from *Myrothecium verrucaria* is commercially available from Amano Enzyme Inc., under the product name of BO "Amano" 3, which is abbreviated as BO-3, and the BO derived from *Bacillus Subtilis* is commercially available from Asahi Kasei Pharma Corporation under the product name of Bilirubin Oxidase, which is abbreviated as BODII, respectively, and these commercially available Bos can also be used in the present invention.

(3) Other Components

Besides the above-mentioned respective components, additional components (optional components) may be contained in the dyeing agent of the present invention. As the optional components, reducing agents such as alkaline compounds, thiolactic acid, sodium sulfite and N-acetyl-L-cysteine, surfactants, oil-based components, silicones, thickening agents, solvents, water, chelating agents, amino acids, various salts, moisturizing agents, antiseptic agents, UV inhibitors, alcohols, polyhydric alcohols, flavor materials and the like can be exemplified.

An alkaline compound may also be incorporated in the dyeing agent of the present invention. According to the dyeing agent containing an alkaline compound, when the dyeing agent is applied, the swelling of the keratin fibers is promoted, and thus the dyeing effect is improved. The incorporation amount of the alkaline compound is preset so that a desired pH (for example, pH 7.0 to 10.0) can be attained for use. An example of the incorporation amount of the one-component type dyeing agent is 0.01 to 20% by weight with respect to the whole amount of the dyeing agent. On the other hand, in the case of the two-component type dyeing agent, in principle, the alkaline compound is incorporated in the first element in which the oxidation dye is to be incorporated, and the incorporation amount is, for example, 0.01 to 20% by weight with respect to the whole amount of the first element (however, the alkaline compound may be incorporated in the second element instead of the first element, or the alkaline compound may be incorporated in both of the first and second elements). In addition, specific examples of the alkaline compound may include amine compounds such as monoethanolamine, monoisopropanolamine, triethanolamine and diethanolamine; and inorganic compounds such as ammonia, sodium hydroxide, potassium hydroxide, ammonium carbonate, sodium carbonate, sodium hydrogen carbonate, potassium carbonate and potassium hydrogen carbonate.

The dyeing agent of the present invention is prepared into a form such as a paste (cream), an aerosol, a gel, a liquid and a foam. In the case of the two-component type consisting of the first element (including the oxidation dye) and the second element (including the BO), the form of the first element is not necessarily the same as that of the second element.

2. Dyeing Method

The second aspect of the present invention relates to a dyeing method using the dyeing agent of the present invention. In the dyeing method of the present invention, the keratin fibers are treated with the dyeing agent of the present invention under a condition in which oxygen is present (namely, under an oxygen atmosphere). In the case of the one-component type dyeing agent, for example, the dyeing agent is diluted as necessary (dilution is not essential), and thereafter applied to the keratin fibers (for example, human hairs). Alternatively, the keratin fibers are immersed in a solution in which the dyeing agent is dissolved.

In the case of the two-component type dyeing agent, for example, the first element and second element are mixed (where necessary, they may be diluted or dissolved in a solvent), and thereafter applied to the keratin fibers. It is also possible to apply one (the first element or second element) to the keratin fibers and thereafter apply the other to the keratin fibers so that the both elements are mixed on the surfaces and the like of the keratin fibers. Alternatively, it is also possible to immerse the keratin fibers in a solution in which the first element and second element are dissolved.

By the operations as mentioned above, a state in which the dyeing agent is contacting with the keratin fibers is formed. Next, the contacting state is maintained for a time required for desired dyeing. At this time, heat retaining or warming is also possible for enhancing the dyeing effect or for rapid or efficient dyeing. In the case when the keratin fibers are human hairs, i.e., for example, in the case when the human hairs are dyed by the dyeing method of the present invention, the contacting state is maintained for about 10 minutes to 2 hours, preferably for about 20 minutes to 1 hour.

The pH condition during the treatment depends on the dyeing agent used. However, it is also possible to adjust the pH by separately using a pH adjusting agent. The pH during the treatment is, for example, pH 7.0 to 9.0. As shown in the following Examples, in the case when the BO was used, a high dyeing effect was shown even under a condition of a relatively low pH. Based on this finding, in an exemplary embodiment of the present invention, the treatment is conducted under a condition of pH 7.0 to 8.0. By adopting this condition, damaging of a material to be dyed in accordance with dyeing can be decreased. This condition is specifically effective in dyeing human hairs, and it becomes possible to decrease damage of human hairs and stimulation to the skin (scalp).

After the above-mentioned treatment, the keratin fibers are generally washed and finally dried. For example, water, a detergent or the like can be used for the washing. As the means for the drying, air drying (natural drying), hot air drying, spin drying, aspiration drying, barrel drying and the like can be exemplified.

In the dyeing method of the present invention, the oxidation and polymerization of the oxidation dye are caused by the action of the BO, thereby the keratin fibers are dyed. In the present invention, since an enzyme is utilized for the oxidation reaction, the damage of the material to be dyed associated with the dyeing treatment is little. Furthermore, the possibilities for adverse effects (allergic response) on the scalp and the like are decreased in the case of an application to the hairs. The dyeing agent of the present invention enables effective dyeing while decreasing the damages of keratin fibers and the like.

EXAMPLES

The dyeing effect of each enzyme in the case when an indole analogue was used as a dye was studied.

1. METHOD (1) Enzymes Used a BO derived from *Myrothecium verrucaria* (Amano Enzyme Inc., product name: BO "Amano" 3, abbreviation: BO-3)

a BO derived from *Bacillus Subtilis* (Asahi Kasei Pharma Corporation, product name: Bilirubin Oxidase, abbreviation: BODII, product code: T-188)

a BO derived from *Trachyderma tsunodae* (Takara Bio Inc., product name: Bilirubin oxidase "TAKARA")

a laccase derived from *Trametes* sp. (Daiwa Fine Chemicals Co., Ltd.)

a laccase derived from *Rhus vernificerea* (Sigma-Aldrich)

(2) Preparation of Hair Dye Base

2% of EMALEX HC-20 (Nihon-Emulsion Co., Ltd.), 1% of lactic acid and oxidation dye agents (5,6-dihydroxyindole, 4-aminoindole and 5-aminoindole) were dissolved by respective predetermined amounts in distilled water, and the pH was adjusted to a predetermined level by using monoethanolamine. Next, 1.5% of hydroxyethyl cellulose was added, mixing was conducted, and distilled water was added so that the final weight can be 80%. Subsequently, an enzyme or hydrogen peroxide was then added to adjust the weight to be 100% in the end.

(3) Hair Dye Test 2 g of the hair dye base was applied per one human white hair bundle (10 cm, 1 g, manufactured by Beaulax) (conducted at n=3). A reaction was conducted at 30° C. for 30 minutes (the bundle was turned over at 15 minutes in midstream). The bundle was washed with water and further washed with 1% SDS, and washing with water was conducted until the color disappeared. Finally, the bundle was left overnight to be air-dried.

(4) Evaluation of Hue

Using a spectrophotometer CM-700d (manufactured by Konica Minolta Optics, Inc.), a measurement was conducted under a visual field of 10°, D65 Day Light and an SCE mode. Using the CIEL*a*b Color System, an evaluation was made based on the color difference from untreated white hairs ($\Delta E^*ab$). L* represents a luminosity value. The value ranges from 0 to 100, and a higher value indicates higher luminance. Furthermore, a* indicates a color. The value ranges from −60 to +60, and the value closer to − indicates stronger green and the value closer to + indicates stronger red. b* indicates a color. The value ranges from −60 to +60, and the value closer to − indicates stronger blue and the value closer to + indicates stronger yellow. $\Delta E^*ab$ is a value calculated by $[(\Delta L)^2 + (\Delta a)^2 + (\Delta b)^2]^{1/2}$ and is a unit that is generally used in the evaluation of hair colors. $\Delta E^*ab$ is calculated by the difference of criterion values (the measured values of the white hairs before dyeing) from the values of L*, a* and b*. The relationship between the degree of the color difference and $\Delta E^*ab$ is shown in Table 1.

TABLE 1

| Critical remarks on degree of color difference | $\Delta E^*ab$ |
| --- | --- |
| Quite slightly differs | 0-0.5 |
| Slightly differs | 0.5-1.5 |
| Differs to detectable degree | 1.5-3.0 |
| Significantly differs | 3.0-6.0 |
| Quite significantly differs | 6.0-12.0 |
| Becomes another color system | 12.0 or more |

2. RESULTS (1) Hair Dye Test 1 (5,6-Dihydroxyindole was Used (0.3% by Weight). The Dyeing was Conducted Under a Condition of pH 7.0.)

The results of the hair dye test 1 are shown in Table 2.

TABLE 2

| | Test Examples | | | | | | | | | | | | | | | | |
|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 |
| 5,6-Dihydroxyindole | | | | | | | | | 0.3 | | | | | | | | |
| EMALEX HC-20 | | | | | | | | | 2 | | | | | | | | |
| Lactic acid | | | | | | | | | 1 | | | | | | | | |
| Carboxyethyl cellulose | | | | | | | | | 1.5 | | | | | | | | |
| BOD II (Asahi Kasei Pharma) | — | — | 0.02 | 0.10 | 0.20 | — | — | — | — | — | — | — | — | — | — | — | — |
| BO-3 (Amano Enzyme) | — | — | — | — | — | 0.01 | 0.05 | 0.10 | — | — | — | — | — | — | — | — | — |
| BO (Takara Bio) | — | — | — | — | — | — | — | — | — | 0.01 | 0.04 | 0.09 | — | — | — | — | — |
| Laccase (Daiwa Fine Chemicals Co., Ltd.) | — | — | — | — | — | — | — | — | — | — | — | — | 0.003 | 0.006 | 0.031 | — | — |
| Laccase (Sigma) | — | — | — | — | — | — | — | — | — | — | — | — | — | — | — | 0.003 | 0.006 | 0.031 |
| $H_2O_2$ | — | 3 | — | — | — | — | — | — | — | — | — | — | — | — | — | — | — |
| Monoethanolamine | | | | | | | | Adjusted to pH 7 | | | | | | | | | |
| Purified water | | | | | | | | Adjusted to 100 g | | | | | | | | | |
| Hair dyeing property ΔE * ab (N = 3; average value) | 5.3 | 12.5 | 33.2 | 28.7 | 25.2 | 13.5 | 18.1 | 17.7 | 11.5 | 10.2 | 9.0 | 6.3 | 6.5 | 7.2 | 7.7 | 6.5 | 10.8 |

Note: Laccase (Sigma) row contains values 0.003, 0.006, 0.031 in columns 15, 16, 17.

As shown in table 2, when the respective enzymes were compared, Test Examples 3 to 5 in which BODII (Asahi Kasei Pharma Corporation) was used and Test Examples 6 to 8 in which BO-3 (Amano Enzyme Inc.) was used indicated higher hair dyeing property than that in Test Examples 1 and 2. Namely, it was found that the BO derived from *Myrothecium verrucaria* and the BO derived from *Bacillus Subtilis* give a higher dyeing effect than hydrogen peroxide does. On the other hand, Test Examples 9 to 17 in which other enzymes were used gave a lower hair dyeing effect than that in the case when hydrogen peroxide was used.

(2) Hair Dye Test 2 (5,6-Dihydroxyindole was Used (0.3% by Weight). The Dyeing was Conducted Under a Condition of pH 9.0.)

The dyeing effects in the cases when dyeing was conducted under an alkaline condition (pH 9.0) were compared. The results are shown in Table 3.

TABLE 3

| | Test Examples | | | | | | | |
|---|---|---|---|---|---|---|---|---|
| | 18 | 19 | 20 | 21 | 22 | 23 | 24 | 25 |
| 5,6-Dihydroxyindole | | | | | 0.3 | | | |
| EMALEX HC-20 | | | | | 2 | | | |
| Lactic acid | | | | | 1 | | | |
| Carboxyethyl cellulose | | | | | 1.5 | | | |
| BOD II (Asahi Kasei Pharma) | — | — | 0.02 | 0.10 | 0.20 | — | — | — |
| BO-3 (Amano Enzyme) | — | — | — | — | — | 0.01 | 0.05 | 0.10 |
| $H_2O_2$ | — | 3 | — | — | — | — | — | — |
| Monoethanolamine | | | | Adjusted to pH 9 | | | | |
| Purified water | | | | Adjusted to 100 g | | | | |
| Hair dyeing property ΔE * ab (N = 3; average value) | 9.2 | 16.3 | 29.6 | 26.6 | 24.5 | 11.9 | 14.6 | 13.4 |

From the comparison between Table 2 and Table 3, it is understood that a higher hair dyeing effect can be obtained when hair dyeing is conducted at pH 7 rather than pH 9 in the cases when BODII or BO-3 is used. Furthermore, the difference between the hair dyeing property by hydrogen peroxide and the hair dyeing property by the BO becomes more significant in the condition of pH 7. From these results, it can be said that hair dyeing under a condition that is gentler to hairs is possible by using the BO.

(3) Hair Dye Test 3 (5,6-Dihydroxyindole was Used (1.0% by Weight). The Dyeing was Conducted Under a Condition of pH 9.0.)

Figure 1:
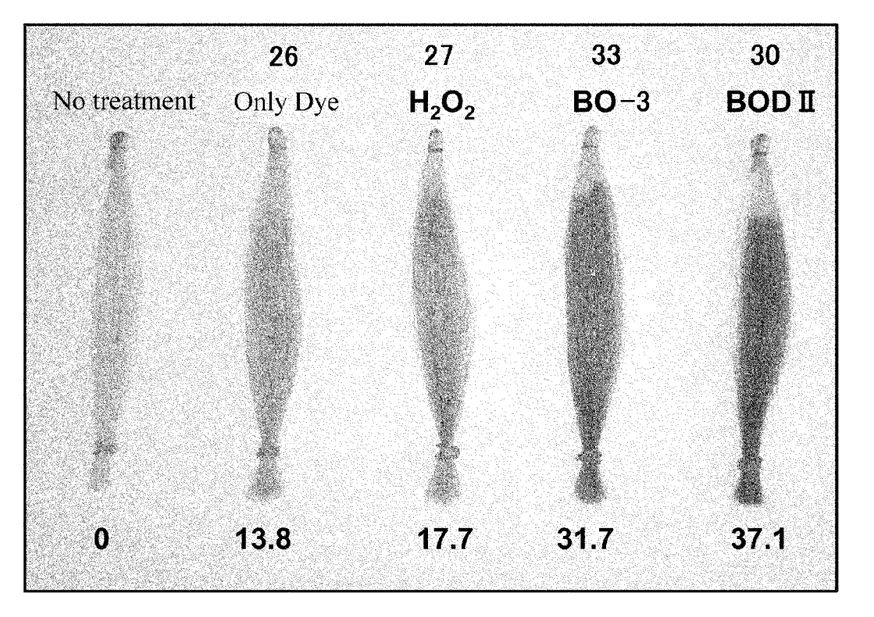
FIG. 1 shows the results of dyeing tests. From the left, the results of the hair dyeing of the non-treated hair bundle (Test Example 27 (only dye), Test Example 28 (hydrogen peroxide), Test Example 34 (BO-3) and Test Example 31 (BODII) are shown. The following numerical values each shows a hair dyeing degree ($\Delta E^*ab$).

The dyeing effects in the cases when the concentration of the oxidation dye agent (5,6-dihydroxyindole) was increased (incorporated by 1.0% by weight with respect to the entirety of the dyeing base) were compared. The results are shown in Table 4 and FIG. 1.

TABLE 4

| | Test Examples | | | | | | | |
|---|---|---|---|---|---|---|---|---|
| | 26 | 27 | 28 | 29 | 30 | 31 | 32 | 33 |
| 5,6-Dihydroxyindole | | | | | 1 | | | |
| EMALEX HC-20 | | | | | 2 | | | |
| Lactic acid | | | | | 1 | | | |
| Carboxyethyl cellulose | | | | | 1.5 | | | |
| BOD II (Asahi Kasei Pharma) | — | — | 0.02 | 0.10 | 0.20 | — | — | — |
| BO-3 (Amano Enzyme) | — | — | — | — | — | 0.01 | 0.05 | 0.10 |
| $H_2O_2$ | — | 3 | — | — | — | — | — | — |
| Monoethanolamine | | | | Adjusted to pH 7 | | | | |
| Purified water | | | | Adjusted to 100 g | | | | |
| Hair dyeing property ΔE * ab (N = 3; average value) | 13.8 | 17.7 | 37.4 | 40.3 | 37.1 | 18.7 | 29.3 | 31.7 |

From the comparison between Test Examples 3 to 5 in Table 1 and Test Examples 28 to 30 in Table 4, and the comparison between Test Examples 6 to 8 in Table 1 and Test Examples 31 to 33 in Table 4, it was indicated that the hair dyeing effect is enhanced by increasing the addition amount of 5,6-dihydroxyindole.

(4) Dyeing Test 4 (Other Indole Derivatives were Used. The Dyeing was Conducted Under a Condition of pH 7.0.)

The dyeing effects in the cases when 4-aminoindole and 5-aminoindole were respectively used as oxidation dye agents were studied. The results are shown in Table 5.

TABLE 5

| | Test Examples | | | | | | | | | | | | | |
|---|---|---|---|---|---|---|---|---|---|---|---|---|---|---|
| | 34 | 35 | 36 | 37 | 38 | 39 | 40 | 41 | 42 | 43 | 44 | 45 | 46 | 47 |
| 4-Aminoindole | | | | | | | | 0.5 | | | | | | |
| 5-Aminoindole | | | | | | | | 0.5 | | | | | | |
| EMALEX HC-20 | | | | | | | | 2 | | | | | | |
| Lactic acid | | | | | | | | 1 | | | | | | |
| Carboxyethyl cellulose | | | | | | | | 1.5 | | | | | | |
| BOD II (Asahi Kasei Pharma) | — | — | 0.02 | 0.10 | 0.20 | — | — | — | | | | | | |
| BO-3 (Amano Enzyme) | — | — | — | — | — | 0.01 | 0.05 | 0.10 | | | | | | |
| Laccase (Daiwa Fine Chemicals Co., Ltd.) | | | | | | | | | 0.003 | 0.006 | 0.031 | | | |
| Laccase (Sigma) | | | | | | | | | | | | 0.003 | 0.006 | 0.031 |
| $H_2O_2$ | — | 3 | — | — | — | — | — | — | | | | | | |
| Monoethanolamine | | | | | | | Adjusted to pH 7 | | | | | | | |
| Purified water | | | | | | | Adjusted to 100 g | | | | | | | |
| Hair dyeing property ΔE*ab (N = 3; average value) | 6.4 | 31.1 | 33.4 | 39.9 | 38.9 | 21.9 | 26.6 | 31.5 | 6.5 | 5.9 | 5.6 | 5.7 | 4.8 | 5.8 |

Also in the cases when 4-aminoindole and 5-aminoindole were used, BODII and BO-3 (Test Examples 36 to 41) indicated dyeing properties equivalent to that of hydrogen peroxide (Test Example 35). On the other hand, hair dyeing effects were not observed for the other enzymes (Test Examples 42 to 47).

3. CONCLUSION

Dyes having high allergic property on the skin (p-phenylenediamine and the like) are currently used in many dyeing agents. Furthermore, since hydrogen peroxide is generally used in the oxidation (color development) of dyes, and hair dye agents are generally used under an alkali condition (typically at pH 9 to 10), the hairs, scalp and the like are easily damaged in accordance with hair dying. It was found by the above study that BOs are effective for dyeing using an indole derivative having low allergic property, and an excellent dyeing effect can be obtained without using hydrogen peroxide. Furthermore, it was found that the BO derived from *Myrothecium verrucaria* and the BO derived from *Bacillus Subtilis* give specifically excellent dyeing effects. On the other hand, it was also found that the BO derived from *Myrothecium verrucaria* and/or the BO derived from *Bacillus Subtilis* finely acts on the indole derivative under a mild condition (pH 7). This fact indicates that these BOs enable hair dyeing under a condition in which damages of hairs, scalps and the like are much smaller, in other words, use of the BOs is extremely advantageous in practical use.

INDUSTRIAL APPLICABILITY

The dyeing agent of the present invention is utilized for dyeing keratin fibers. Specifically, the present invention is effective for hair dyeing.

This invention is not limited at all by the above-mentioned embodiments for carrying out the invention and the explanations in Examples. Various modifications are also encompassed in this invention within the scope that does not deviate from the descriptions in the claims and can be easily conceived by persons skilled in the art. The whole contents of the articles, patent publications, patents, and the like which are clearly indicated in the present specification are incorporated herein by reference.

The invention claimed is:

1. A dyeing agent for dyeing keratin fibers, comprising:
0.3-1% by weight of 5,6-dihydroxyindole or 5,6-dihydroxyindoline as oxidation dyeing agents with a pH in a range of 7.0 to 9.0, and 0.02-0.2% by weight of a bilirubin oxidase (EC1.3.3.5) derived from *Bacillus subtilis*; or
1.0% by weight of 4-aminoindole and 5-aminoindole as oxidation dyeing agents with a pH of 7.0 and 0.02-0.2% by weight of the bilirubin oxidase derived from *Bacillus subtilis*.

2. The dyeing agent according to claim 1, wherein the bilirubin oxidase is consisting of a protein described in any of the following (7) to (9):
(7) a protein consisting of the amino acid sequence of SEQ ID NO: 6;
(8) a protein consisting of an amino acid sequence in which one or several amino acid(s) is/are mutated, deleted or added in the amino acid sequence of SEQ ID NO: 6, which has a bilirubin oxidase activity;
(9) a protein that is encoded by the polynucleotide of SEQ ID NO: 5.

3. The dyeing agent according to claim 1, wherein the keratin fibers are human hairs.

4. The dyeing agent according to claim 1, which is a one-component form containing the oxidation dyeing agent and the bilirubin oxidase.

5. The dyeing agent according to claim 1, which is a two-component type consisting of a first element containing the oxidation dyeing agent and a second element containing the bilirubin oxidase.

6. The dyeing agent according to claim 2, wherein the keratin fibers are human hairs.

7. The dyeing agent according to claim 2, which is a one-component form containing the oxidation dyeing agent and the bilirubin oxidase.

8. The dyeing agent according to claim 3, which is a one-component form containing the oxidation dyeing agent and the bilirubin oxidase.

9. The dyeing agent according to claim 2, which is a two-component type consisting of a first element containing the oxidation dyeing agent and a second element containing the bilirubin oxidase.

10. The dyeing agent according to claim 3, which is a two-component type consisting of a first element containing the oxidation dyeing agent and a second element containing the bilirubin oxidase.

11. The dyeing agent for dyeing keratin fibers according to claim 1, wherein the 1.0% by weight of 4-aminoindole and 5-aminoindole is 0.5% by weight of 4-aminoindole and 0.5% by weight of 5-aminoindole.

12. A dyeing method, comprising a step of treating keratin fibers with the dyeing agent according to claim 1.

13. A dyeing method, comprising a step of treating keratin fibers with the dyeing agent according to claim 2.

14. A dyeing method, comprising a step of treating keratin fibers with the dyeing agent according to claim 3.

* * * * *

SEQUENCE LISTING

```
<160> NUMBER OF SEQ ID NOS: 6

<210> SEQ ID NO 1
<211> LENGTH: 1719
<212> TYPE: DNA
<213> ORGANISM: Myrothecium verrucaria

<400> SEQUENCE: 1
atgttcaaac acacacttgg agctgctgcc ctcagcttgc ttttcaacag caatgctgtc      60
caggcaagcc ccgtccccga gacctcaccg gcaactggac atctcttcaa gcgagttgcc     120
cagatcagcc cacagtatcc catgttcaca gtaccactgc caattcctcc tgttaagcag     180
ccccgcttga ctgtaaccaa tcctgtgaat ggacaagaga tctggtacta tgaggtcgag     240
atcaagccct tcactcacca ggtttaccct gaccttggat ccgctgatct ggtcgggtat     300
gatggaatgt ctcctggccc tactttccag gttcctcgtg gagttgaaac agttgtccgc     360
ttcattaaca atgctgaggc tcctaactcc gttcacctgc acggatcatt ctctcgtgcc     420
```

```
gcctttgacg gatgggcaga ggacatcacc gagcctggca gcttcaaaga ctattactac    480
ccaaatagac agtctgctcg taccctatgg taccacgatc atgctatgca tatcactgct    540
gagaacgcct accgtggcca ggctggtctc tacatgctca ctgacccagc cgaagacgct    600
ctcaacttgc caagtggata tggcgagttc gatattccaa tgatcctcac gtccaagcaa    660
tataccgcaa acggcaactt ggtcaccact aatggagagc tgaactcatt ctggggtgat    720
gtaattcacg tgaacggtca accctggcct tcaagaacg ttgagcctcg caaatatcga    780
ttccgcttcc tcgatgccgc agtttctcgc tctttcggcc tttactttgc tgatactgat    840
gctatcgaca ctcgcttgcc tttcaaggtt attgcctccg attctggtct tcttgaacac    900
cctgccgata ccagcttgct gtacatttcc atggccgagc gttacgaagt tgtgtttgac    960
ttctccgact atgctggcaa gactattgaa ctccgcaacc tgggcggtag cattggcggc   1020
atcggaacag ataccgacta tgacaacacc gacaaggtca tgcgtttcgt ggtagcagac   1080
gacacaactc agccagatac ctcagttgtt cctgctaacc ttcgtgatgt tcccttcccc   1140
tctcccacca caaacacccc ccgacagttc cgctttggtc gcaccggtcc tacctggact   1200
attaatggtg ttgcttttgc tgatgttcaa aaccgtctgc ttgcaaacgt acccgttggt   1260
actgtcgagc gttgggagct catcaacgcc ggtaacggtt ggacgcaccc tattcacatc   1320
catcttgtcg acttcaaggt gatttctcgt acttccggca caacgcgcg cacagtcatg   1380 ccatacgagt ccggtctcaa agacgttgtc tggcttggtc gccgtgaaac tgtggttgtt   1440
gaggctcatt acgcgccttt ccctggtgta tacatgttcc attgccacaa tttgattcac   1500
gaggatcacg atatgatggc tgcctttaac gccaccgtcc tgccagatta tggctataat   1560
gccactgttt tcgttgaccc tatggaagag ctttggcagg ctcgtcctta tgaactcggc   1620
gagttccagg ctcagagtgg ccagttcagc gttcaggctg ttactgagcg tattcagact   1680
atggctgaat acagacctta cgccgcagct gacgagtag                          1719
```

<210> SEQ ID NO 2
<211> LENGTH: 572
<212> TYPE: PRT
<213> ORGANISM: Myrothecium verrucaria

<400> SEQUENCE: 2

```
Met Phe Lys His Thr Leu Gly Ala Ala Ala Leu Ser Leu Leu Phe Asn
1               5                   10                  15

Ser Asn Ala Val Gln Ala Ser Pro Val Pro Glu Thr Ser Pro Ala Thr
            20                  25                  30

Gly His Leu Phe Lys Arg Val Ala Gln Ile Ser Pro Gln Tyr Pro Met
        35                  40                  45

Phe Thr Val Pro Leu Pro Ile Pro Pro Val Lys Gln Pro Arg Leu Thr
    50                  55                  60

Val Thr Asn Pro Val Asn Gly Gln Glu Ile Trp Tyr Tyr Glu Val Glu
65                  70                  75                  80

Ile Lys Pro Phe Thr His Gln Val Tyr Pro Asp Leu Gly Ser Ala Asp
                85                  90                  95

Leu Val Gly Tyr Asp Gly Met Ser Pro Gly Pro Thr Phe Gln Val Pro
            100                 105                 110

Arg Gly Val Glu Thr Val Val Arg Phe Ile Asn Asn Ala Glu Ala Pro
        115                 120                 125

Asn Ser Val His Leu His Gly Ser Phe Ser Arg Ala Ala Phe Asp Gly
    130                 135                 140
```

```
Trp Ala Glu Asp Ile Thr Glu Pro Gly Ser Phe Lys Asp Tyr Tyr Tyr
145                 150                 155                 160

Pro Asn Arg Gln Ser Ala Arg Thr Leu Trp Tyr His Asp His Ala Met
            165                 170                 175

His Ile Thr Ala Glu Asn Ala Tyr Arg Gly Gln Ala Gly Leu Tyr Met
            180                 185                 190

Leu Thr Asp Pro Ala Glu Asp Ala Leu Asn Leu Pro Ser Gly Tyr Gly
        195                 200                 205

Glu Phe Asp Ile Pro Met Ile Leu Thr Ser Lys Gln Tyr Thr Ala Asn
        210                 215                 220

Gly Asn Leu Val Thr Thr Asn Gly Glu Leu Asn Ser Phe Trp Gly Asp
225                 230                 235                 240

Val Ile His Val Asn Gly Gln Pro Trp Pro Phe Lys Asn Val Glu Pro
            245                 250                 255

Arg Lys Tyr Arg Phe Arg Phe Leu Asp Ala Ala Val Ser Arg Ser Phe
            260                 265                 270

Gly Leu Tyr Phe Ala Asp Thr Asp Ala Ile Asp Thr Arg Leu Pro Phe
            275                 280                 285

Lys Val Ile Ala Ser Asp Ser Gly Leu Leu Glu His Pro Ala Asp Thr
290                 295                 300

Ser Leu Leu Tyr Ile Ser Met Ala Glu Arg Tyr Glu Val Val Phe Asp
305                 310                 315                 320

Phe Ser Asp Tyr Ala Gly Lys Thr Ile Glu Leu Arg Asn Leu Gly Gly
            325                 330                 335

Ser Ile Gly Gly Ile Gly Thr Asp Thr Asp Tyr Asp Asn Thr Asp Lys
            340                 345                 350

Val Met Arg Phe Val Val Ala Asp Asp Thr Thr Gln Pro Asp Thr Ser
            355                 360                 365

Val Val Pro Ala Asn Leu Arg Asp Val Pro Phe Pro Ser Pro Thr Thr
        370                 375                 380

Asn Thr Pro Arg Gln Phe Arg Phe Gly Arg Thr Gly Pro Thr Trp Thr
385                 390                 395                 400

Ile Asn Gly Val Ala Phe Ala Asp Val Gln Asn Arg Leu Leu Ala Asn
            405                 410                 415

Val Pro Val Gly Thr Val Glu Arg Trp Glu Leu Ile Asn Ala Gly Asn
            420                 425                 430

Gly Trp Thr His Pro Ile His Ile His Leu Val Asp Phe Lys Val Ile
            435                 440                 445

Ser Arg Thr Ser Gly Asn Asn Ala Arg Thr Val Met Pro Tyr Glu Ser
450                 455                 460

Gly Leu Lys Asp Val Val Trp Leu Gly Arg Arg Glu Thr Val Val Val
465                 470                 475                 480

Glu Ala His Tyr Ala Pro Phe Pro Gly Val Tyr Met Phe His Cys His
            485                 490                 495

Asn Leu Ile His Glu Asp His Asp Met Met Ala Ala Phe Asn Ala Thr
            500                 505                 510

Val Leu Pro Asp Tyr Gly Tyr Asn Ala Thr Val Phe Val Asp Pro Met
            515                 520                 525

Glu Glu Leu Trp Gln Ala Arg Pro Tyr Glu Leu Gly Glu Phe Gln Ala
        530                 535                 540

Gln Ser Gly Gln Phe Ser Val Gln Ala Val Thr Glu Arg Ile Gln Thr
545                 550                 555                 560
```

Met Ala Glu Tyr Arg Pro Tyr Ala Ala Ala Asp Glu
            565                 570

<210> SEQ ID NO 3
<211> LENGTH: 1605
<212> TYPE: DNA
<213> ORGANISM: Myrothecium verrucaria

<400> SEQUENCE: 3

| | | | | | |
|---|---|---|---|---|---|
| gttgcccaga | tcagcccaca | gtatcccatg | ttcacagtac | cactgccaat | tcctcctgtt | 60 |
| aagcagcccc | gcttgactgt | aaccaatcct | gtgaatggac | aagagatctg | gtactatgag | 120 |
| gtcgagatca | agcccttcac | tcaccaggtt | taccctgacc | ttggatccgc | tgatctggtc | 180 |
| gggtatgatg | gaatgtctcc | tggccctact | ttccaggttc | ctcgtggagt | tgaaacagtt | 240 |
| gtccgcttca | ttaacaatgc | tgaggctcct | aactccgttc | acctgcacgg | atcattctct | 300 |
| cgtgccgcct | ttgacggatg | gcagaggac | atcaccgagc | tggcagcttt | caaagactat | 360 |
| tactacccaa | atagacagtc | tgctcgtacc | ctatggtacc | acgatcatgc | tatgcatatc | 420 |
| actgctgaga | acgcctaccg | tggccaggct | ggtctctaca | tgctcactga | cccagccgaa | 480 |
| gacgctctca | acttgccaag | tggatatggc | gagttcgata | ttccaatgat | cctcacgtcc | 540 |
| aagcaatata | ccgcaaacgg | caacttggtc | accactaatg | gagagctgaa | ctcattctgg | 600 |
| ggtgatgtaa | ttcacgtgaa | cggtcaaccc | tggccttttca | agaacgttga | gcctcgcaaa | 660 |
| tatcgattcc | gcttcctcga | tgccgcagtt | tctcgctctt | tcggcctttta | ctttgctgat | 720 |
| actgatgcta | tcgacactcg | cttgcctttc | aaggttattg | cctccgattc | tggtcttctt | 780 |
| gaacaccctg | ccgataccag | cttgctgtac | atttccatgg | ccgagcgtta | cgaagttgtg | 840 |
| tttgacttct | ccgactatgc | tggcaagact | attgaactcc | gcaacctggg | cggtagcatt | 900 |
| ggcggcatcg | gaacagatac | cgactatgac | aacaccgaca | aggtcatgcg | tttcgtggta | 960 |
| gcagacgaca | caactcagcc | agatacctca | gttgttcctg | ctaaccttcg | tgatgttccc | 1020 |
| ttcccctctc | ccaccacaaa | cacccccga | cagttccgct | ttggtcgcac | cggtcctacc | 1080 |
| tggactatta | atggtgttgc | ttttgctgat | gttcaaaacc | gtctgcttgc | aaacgtaccc | 1140 |
| gttggtactg | tcgagcgttg | ggagctcatc | aacgccggta | acggttggac | gcaccctatt | 1200 |
| cacatccatc | ttgtcgactt | caaggtgatt | tctcgtactt | ccggcaacaa | cgcgcgcaca | 1260 |
| gtcatgccat | acgagtccgg | tctcaaagac | gttgtctggc | ttggtcgccg | tgaaactgtg | 1320 |
| gttgttgagg | ctcattacgc | gcctttccct | ggtgtataca | tgttccattg | ccacaatttg | 1380 |
| attcacgagg | atcacgatat | gatggctgcc | tttaacgcca | ccgtcctgcc | agattatggc | 1440 |
| tataatgcca | ctgttttcgt | tgaccctatg | gaagagcttt | ggcaggctcg | tccttatgaa | 1500 |
| ctcggcgagt | tccaggctca | gagtggccag | ttcagcgttc | aggctgttac | tgagcgtatt | 1560 |
| cagactatgg | ctgaatacag | accttacgcc | gcagctgacg | agtag | | 1605 |

<210> SEQ ID NO 4
<211> LENGTH: 534
<212> TYPE: PRT
<213> ORGANISM: Myrothecium verrucaria

<400> SEQUENCE: 4

Val Ala Gln Ile Ser Pro Gln Tyr Pro Met Phe Thr Val Pro Leu Pro
1               5                   10                  15

Ile Pro Pro Val Lys Gln Pro Arg Leu Thr Val Thr Asn Pro Val Asn
            20                  25                  30

-continued

```
Gly Gln Glu Ile Trp Tyr Tyr Glu Val Ile Lys Pro Phe Thr His
        35                  40              45

Gln Val Tyr Pro Asp Leu Gly Ser Ala Asp Leu Val Gly Tyr Asp Gly
    50                  55                  60

Met Ser Pro Gly Pro Thr Phe Gln Val Pro Arg Gly Val Glu Thr Val
65                  70                  75                  80

Val Arg Phe Ile Asn Asn Ala Glu Ala Pro Asn Ser Val His Leu His
                85                  90                  95

Gly Ser Phe Ser Arg Ala Ala Phe Asp Gly Trp Ala Glu Asp Ile Thr
                100                 105                 110

Glu Pro Gly Ser Phe Lys Asp Tyr Tyr Pro Asn Arg Gln Ser Ala
                115                 120                 125

Arg Thr Leu Trp Tyr His Asp His Ala Met His Ile Thr Ala Glu Asn
                130                 135                 140

Ala Tyr Arg Gly Gln Ala Gly Leu Tyr Met Leu Thr Asp Pro Ala Glu
145                 150                 155                 160

Asp Ala Leu Asn Leu Pro Ser Gly Tyr Gly Glu Phe Asp Ile Pro Met
                165                 170                 175

Ile Leu Thr Ser Lys Gln Tyr Thr Ala Asn Gly Asn Leu Val Thr Thr
                180                 185                 190

Asn Gly Glu Leu Asn Ser Phe Trp Gly Asp Val Ile His Val Asn Gly
                195                 200                 205

Gln Pro Trp Pro Phe Lys Asn Val Glu Pro Arg Lys Tyr Arg Phe Arg
                210                 215                 220

Phe Leu Asp Ala Ala Val Ser Arg Ser Phe Gly Leu Tyr Phe Ala Asp
225                 230                 235                 240

Thr Asp Ala Ile Asp Thr Arg Leu Pro Phe Lys Val Ile Ala Ser Asp
                245                 250                 255

Ser Gly Leu Leu Glu His Pro Ala Asp Thr Ser Leu Leu Tyr Ile Ser
                260                 265                 270

Met Ala Glu Arg Tyr Glu Val Val Phe Asp Phe Ser Tyr Ala Gly
                275                 280                 285

Lys Thr Ile Glu Leu Arg Asn Leu Gly Gly Ser Ile Gly Gly Ile Gly
                290                 295                 300

Thr Asp Thr Asp Tyr Asp Asn Thr Asp Lys Val Met Arg Phe Val Val
305                 310                 315                 320

Ala Asp Asp Thr Thr Gln Pro Asp Thr Ser Val Val Pro Ala Asn Leu
                325                 330                 335

Arg Asp Val Pro Phe Pro Ser Pro Thr Thr Asn Thr Pro Arg Gln Phe
                340                 345                 350

Arg Phe Gly Arg Thr Gly Pro Thr Trp Thr Ile Asn Gly Val Ala Phe
                355                 360                 365

Ala Asp Val Gln Asn Arg Leu Leu Ala Asn Val Pro Val Gly Thr Val
                370                 375                 380

Glu Arg Trp Glu Leu Ile Asn Ala Gly Asn Gly Trp Thr His Pro Ile
385                 390                 395                 400

His Ile His Leu Val Asp Phe Lys Val Ile Ser Arg Thr Ser Gly Asn
                405                 410                 415

Asn Ala Arg Thr Val Met Pro Tyr Glu Ser Gly Leu Lys Asp Val Val
                420                 425                 430

Trp Leu Gly Arg Arg Glu Thr Val Val Val Glu Ala His Tyr Ala Pro
                435                 440                 445
```

```
Phe Pro Gly Val Tyr Met Phe His Cys His Asn Leu Ile His Glu Asp
    450                 455                 460
His Asp Met Met Ala Ala Phe Asn Ala Thr Val Leu Pro Asp Tyr Gly
465                 470                 475                 480
Tyr Asn Ala Thr Val Phe Val Asp Pro Met Glu Glu Leu Trp Gln Ala
                485                 490                 495
Arg Pro Tyr Glu Leu Gly Glu Phe Gln Ala Gln Ser Gly Gln Phe Ser
            500                 505                 510
Val Gln Ala Val Thr Glu Arg Ile Gln Thr Met Ala Glu Tyr Arg Pro
        515                 520                 525
Tyr Ala Ala Ala Asp Glu
    530

<210> SEQ ID NO 5
<211> LENGTH: 1702
<212> TYPE: DNA
<213> ORGANISM: Bacillus subtilis

<400> SEQUENCE: 5
gaagattttt tgtaaccatc acgtccttat tgtcattaac tatagtacca atttggaaaa      60
tttagataag gacagatgaa aatgacactt gaaaaatttg tggatgctct cccaatccca     120
gatacactaa agccagtaca gcaatcaaaa gaaaaaacat actacgaagt caccatggag     180
gaatgcactc atcagctcca tcgcgatctc cctccaaccc gctgtgggg  ctacaacggc     240 ttatttccgg gaccgaccat tgaggttaaa agaaatgaaa acgtatatgt aaaatggatg     300
aataaccttc cttccacgca tttccttccg attgatcaca ccattcatca cagtgacagc     360
cagcatgaag agcccgaggt aaagactgtt gttcatttac acggcggcgt cacgccagat     420
gatagtgacg ggtatccgga ggcttggttt tccaaagact tgaacaaaac aggaccttat     480
ttcaaaagag aggtttatca ttatccaaac cagcagcgcg gggctatatt gtggtatcac     540
gatcacgcca tggcgctcac caggctaaat gtctatgccg acttgtcgg tgcatatatc     600 attcatgacc caaggaaaa acgcttaaaa ctgccttcag acgaatacga tgtgccgctt     660
cttatcacag accgcacgat caatgaggat ggttctttgt tttatccgag cgcaccggaa     720 aaccccttctc cgtcactgcc taatccttca atcgttccgg cttttgcgg agaaaccata     780 ctcgtcaacg ggaaggtatg gccatacttg aagtcgagc caaggaaata ccgattccgt     840
gtcatcaacg cctccaatac aagaacctat aacctgtcac tcgataatgg cggagatttt     900
attcagattg gttcagatgg agggctcctg ccgcgatctg ttaaactgaa ttcttttcagc     960 cttgcgcctg ctgaacgtta cgatatcatc attgacttca cagcatatga aggagaatcg    1020
atcattttgg caaacagcgc gggctgcggc ggtgacgtca atcctgaaac agatgcgaat    1080
atcatgcaat tcagagtcac aaaaccattg gcacaaaaag acgaaagcag aaagccgaag    1140
tacctcgcct catacccttc ggtacagcat gaaagaatac aaaacatcag aacgttaaaa    1200
ctggcaggca cccaggacga atacggcaga cccgtccttc tgcttaataa caaacgctgg    1260
cacgatcccg tcacagaaac accaaaagtc ggcacaactg aaatatggtc cattatcaac    1320
ccgacacgcg gaacacatcc gatccacctg catctagtct ccttccgtgt attagaccgg    1380
cggccgtttg atatcgcccg ttatcaagaa agcggggaat tgtcctatac cggtccggct    1440
gtcccgccgc cgccaagtga aaagggctgg aaagacacca ttcaagcgca tgcaggtgaa    1500
gtcctgagaa tcgcggcgac attcggtccg tacagcggac gatacgtatg gcattgccat    1560
attctagagc atgaagacta tgacatgatg agaccgatgg atataactga tcccccataaa   1620
```

```
taacccgaca aacttgcctc tagcaggcaa gttttttctt tatgaaacct ttggccctat   1680
ttatcgtatt acgtaaaaac aa                                            1702
```

<210> SEQ ID NO 6
<211> LENGTH: 515
<212> TYPE: PRT
<213> ORGANISM: Bacillus subtilis

<400> SEQUENCE: 6

```
Met Lys Met Thr Leu Glu Lys Phe Val Asp Ala Leu Pro Ile Pro Asp
1               5                   10                  15

Thr Leu Lys Pro Val Gln Gln Ser Lys Glu Lys Thr Tyr Tyr Glu Val
            20                  25                  30

Thr Met Glu Glu Cys Thr His Gln Leu His Arg Asp Leu Pro Pro Thr
        35                  40                  45

Arg Leu Trp Gly Tyr Asn Gly Leu Phe Pro Gly Pro Thr Ile Glu Val
    50                  55                  60

Lys Arg Asn Glu Asn Val Tyr Val Lys Trp Met Asn Asn Leu Pro Ser
65                  70                  75                  80

Thr His Phe Leu Pro Ile Asp His Thr Ile His His Ser Asp Ser Gln
                85                  90                  95

His Glu Glu Pro Glu Val Lys Thr Val Val His Leu His Gly Gly Val
            100                 105                 110

Thr Pro Asp Asp Ser Asp Gly Tyr Pro Glu Ala Trp Phe Ser Lys Asp
        115                 120                 125

Phe Glu Gln Thr Gly Pro Tyr Phe Lys Arg Glu Val Tyr His Tyr Pro
    130                 135                 140

Asn Gln Gln Arg Gly Ala Ile Leu Trp Tyr His Asp His Ala Met Ala
145                 150                 155                 160

Leu Thr Arg Leu Asn Val Tyr Ala Gly Leu Val Gly Ala Tyr Ile Ile
                165                 170                 175

His Asp Pro Lys Glu Lys Arg Leu Lys Leu Pro Ser Asp Glu Tyr Asp
            180                 185                 190

Val Pro Leu Leu Ile Thr Asp Arg Thr Ile Asn Glu Asp Gly Ser Leu
        195                 200                 205

Phe Tyr Pro Ser Ala Pro Glu Asn Pro Ser Pro Ser Leu Pro Asn Pro
    210                 215                 220

Ser Ile Val Pro Ala Phe Cys Gly Glu Thr Ile Leu Val Asn Gly Lys
225                 230                 235                 240

Val Trp Pro Tyr Leu Glu Val Glu Pro Arg Lys Tyr Arg Phe Arg Val
                245                 250                 255

Ile Asn Ala Ser Asn Thr Arg Thr Tyr Asn Leu Ser Leu Asp Asn Gly
            260                 265                 270

Gly Asp Phe Ile Gln Ile Gly Ser Asp Gly Gly Leu Leu Pro Arg Ser
        275                 280                 285

Val Lys Leu Asn Ser Phe Ser Leu Ala Pro Ala Glu Arg Tyr Asp Ile
    290                 295                 300

Ile Ile Asp Phe Thr Ala Tyr Glu Gly Glu Ser Ile Ile Leu Ala Asn
305                 310                 315                 320

Ser Ala Gly Cys Gly Gly Asp Val Asn Pro Glu Thr Asp Ala Asn Ile
                325                 330                 335

Met Gln Phe Arg Val Thr Lys Pro Leu Ala Gln Lys Asp Glu Ser Arg
            340                 345                 350
```

-continued

```
Lys Pro Lys Tyr Leu Ala Ser Tyr Pro Ser Val Gln His Glu Arg Ile
        355                 360                 365
Gln Asn Ile Arg Thr Leu Lys Leu Ala Gly Thr Gln Asp Glu Tyr Gly
    370                 375                 380
Arg Pro Val Leu Leu Asn Asn Lys Arg Trp His Asp Pro Val Thr
385                 390                 395                 400
Glu Thr Pro Lys Val Gly Thr Thr Glu Ile Trp Ser Ile Ile Asn Pro
                405                 410                 415
Thr Arg Gly Thr His Pro Ile His Leu His Leu Val Ser Phe Arg Val
            420                 425                 430
Leu Asp Arg Arg Pro Phe Asp Ile Ala Arg Tyr Gln Glu Ser Gly Glu
        435                 440                 445
Leu Ser Tyr Thr Gly Pro Ala Val Pro Pro Pro Ser Glu Lys Gly
    450                 455                 460
Trp Lys Asp Thr Ile Gln Ala His Ala Gly Glu Val Leu Arg Ile Ala
465                 470                 475                 480
Ala Thr Phe Gly Pro Tyr Ser Gly Arg Tyr Val Trp His Cys His Ile
                485                 490                 495
Leu Glu His Glu Asp Tyr Asp Met Met Arg Pro Met Asp Ile Thr Asp
            500                 505                 510
Pro His Lys
        515
```